United States Patent [19]
Morgan

[11] Patent Number: 5,814,048
[45] Date of Patent: Sep. 29, 1998

[54] CRANIOPLASTY PLATES AND METHOD OF INSTALLATION

[75] Inventor: Frank H. Morgan, Las Vegas, Nev.

[73] Assignee: Sofamor Danek Properties, Inc., Memphis, Tenn.

[21] Appl. No.: 642,648

[22] Filed: May 3, 1996

[51] Int. Cl.⁶ .................................................. A61B 17/80
[52] U.S. Cl. ......................................................... 606/69
[58] Field of Search ................................ 606/69, 70, 71, 606/72, 73, 60, 101, 86

[56] References Cited

U.S. PATENT DOCUMENTS

| | | | |
|---|---|---|---|
| 3,643,658 | 2/1972 | Steinemenan | 606/69 |
| 5,139,497 | 8/1992 | Tilghman et al. | 606/69 |
| 5,201,737 | 4/1993 | Leibinger et al. | 606/69 |
| 5,346,492 | 9/1994 | Morgan | 606/60 |
| 5,372,598 | 12/1994 | Luhr et al. | 606/69 |

OTHER PUBLICATIONS

Geib, Fred W., "Vitallium Skull Plates", Journal of Amer. Med. Assoc., vol. 117, Jul. 1941, pp. 8–12.

Primary Examiner—Guy V. Tucker
Attorney, Agent, or Firm—Woodard, Emhardt, Naughton Moriarty & McNett

[57] ABSTRACT

A biocompatible cranioplasty plate structure, and method of its installation, for use in the surgical repair and recontour of large cranial defects of the human skull created or caused by injury, surgical intervention for tumor removal, or congenital anomaly or disease. The plate structure is formed from a sheet of pliable perforated metallic material, particularly commercially pure titanium or titanium alloy material, and is of generally elliptical configuration with a central preformed arcuate and convex area matching the compound and complex curvature of the forehead, side or rear areas of the typical human adult skull. The plate structure includes adjustable peripheral panels for bending fitment and close adaptation of the plate structure to intact cranial bone of the skull adjacent to and surrounding the defect and for attachment of the plate structure to intact bone by bone screws having low profile heads and applicable through perforations of the peripheral panels. The perforated metallic sheet material may be a mesh material having parallel rows and perpendicularly arranged parallel lines of square or circular holes. Alternatively, the perforated metallic sheet material may be a gridwork including legs which define repeating patterns of rectangular or triangular open spaces.

12 Claims, 4 Drawing Sheets

CRANIOPLASTY PLATES AND METHOD OF INSTALLATION

FIELD OF THE INVENTION

The present invention relates to perforated metallic plates for use in the surgical repair and recontour of the human skull following a depressed fracture, an intracranial operation for tumor removal, or a penetrating missile injury, or to correct a congenital skull defect.

BACKGROUND OF THE INVENTION

One of the most conspicuous and psychologically distressful after effects of a depressed fracture of the skull, an intracranial tumor operation, a penetrating missile injury, or life with a congenital skull deformity is a disfiguring skull defect. Frontal defects are usually unsightly and cause discomfort, especially when the patient bends forward. Also, patients with large cranial defects feel insecure because of the brain's vulnerability to trauma.

In anatomic descriptions, the skull is commonly divided into: 1) the cranium or "braincase" which encloses the brain and is comprised of eight bones; and 2) the skeleton of the face comprised of twelve paired bones. The eight bones that form the cranium include: the lower rear occipital bone, the sphenoid bone forming the back of the eye sockets, the ethmoid bone forming the inner part of the eye sockets, the frontal bone forming the forehead, the right and left side temporal bones, and the right and left side parietal bones contributing to the sides and base of the skull. The separate bones of the cranium are held together by immovable joints called sutures found only between the skull bones.

When viewed from without, the cranium is generally spheroidal in shape which is divisible into six regions, namely,: "superior" (vertex or dome region), right and left "lateral", "posterior" (occipital bone region), "anterior" (frontal bone region), and "inferior" (base region). Viewed from above, the skull is oval in outline (wider behind than in front) and defined by the right and left side parietal bones, the greater part of the frontal bone, the distal portions or wings of the sphenoid bone, the right and left temporal bones, and the lower rear occipital bone. The arcuate and convex shaped areas encompassing: 1) the anterior frontal bone, 2) the right and left side parietal and temporal bones, and 3) the occipital bone and posterior portions of the right and left side parietal bones are reasonably alike in size and curvature for the typical adult human males and for the typical adult human females. These skull areas form the principal fields for the occurrence of depressed fractures, penetrating missile injuries, and intracranial tumor surgical procedures. Such areas also form the principal fields for the surgical correction of congenital skull defects.

Various cranioplasty methods and materials have been employed over many years for the repair of skull defects. A satisfactory cranioplasty procedure should employ an onlay technique with a simple method of attachment of the prosthesis to the skull. The material used should be biologically inert with respect to the tissues it contacts, radiolucent, easily and accurately shaped to the normal skull contour in the area of application, capable of being adjusted at the time of application, and it should have sufficient mechanical strength to resist fracture or deformation under severe impact loading.

After World War I autogenous bone grafts, taken from the iliac crest, were used as the material of choice for cranioplasty procedures. A major operation was required to obtain the graft for a large skull defect and the patients often had more postoperative pain from the donor site than from the actual grafted skull area. Further, reproduction of the appropriate skull contour often proved to be difficult.

Following World War II some skull defects were repaired through the use of autopolymerized acrylic resin plates. Initially, such cranioplasty plates were preformed from a template or impression made at the time of a first operation. Later, form-fitting plastic cranioplasty procedures were tried in which the plastic material was molded into the skull defect during the plastic hardening process—the hardening process frequently releasing excess heat both to the patient at the cranioplasty site and to the hands of the surgeon shaping the material within the defect. Again, with larger defects, it was found to be difficult to shape and appropriately contour the cranioplasty material.

Metals and metal alloys, including tantalum, titanium, stainless steel, and chromium-cobalt, have not been widely used because of the difficulty in forming the cranioplasty plate to the compound and complex curvatures of the skull. Tantalum cranioplasty plates have been shaped by die swaging techniques or by hammering tantalum plate material into a counter die.

For treating small skull defects the use of plastic or metal cranioplasty plates or bone-grafting techniques have usually proved satisfactory. The larger skull defect, however, has posed the special problem of matching cranioplasty plates to skull contours and of fixation of such plates to adjacent skull bone structures.

It is a principal object of the present invention to provide perforated titanium cranioplasty plates for the surgical repair and recontour of large defects of the human skull.

It is a further object of the invention to provide perforated titanium cranioplasty plates for the surgical repair and recontour of large defects of the human adult skull with such plates having a central preformed convex area matching the compound and complex curvatures of forehead, side and rear areas of the typical human adult skull.

It is a still further object of the invention to provide perforated titanium cranioplasty plates for the surgical repair and recontour of large defects of the human adult skull with such plates having a central preformed convex area matching the compound and complex curvatures of the forehead, side and rear areas of the typical human adult skull and having adjustable (pliable) peripheral panels for fitment and attachment of the plates to normal cranial bone structures adjacent the defects.

Other objects and advantages of the invention will become apparent from the following summary and detailed descriptions of the preferred embodiments of the invention taken in conjunction with the accompanying drawing figures.

SUMMARY OF THE INVENTION

The present invention relates to improved metallic cranioplasty plates for use in the surgical repair and recontour of large cranial defects of the human skull resulting from a depressed fracture of the skull, an intracranial tumor removal operation, a penetrating missile injury to the skull, or a congenital skull deformity. More specifically, the invention relates to the provision of large cranioplasty plates fabricated from relatively thin perforated, biologically inert, titanium sheet material having a shape and size sufficient to completely cover the cranial defect area and including pliable slotted peripheral attachment panels for final contouring and fitment of the plates to the skull for close cranial adaptation thereto.

The perforated titanium cranioplasty plates of the invention include a preformed arcuate and convex central area within the confines of the pliable peripheral attachment panels. The convex central areas of the plates are of a size and curvature shape which reasonably match the spheroidal shape and size of the skulls of the majority of adult human male patients and adult human female patients. Thus, the arcuate and convex shaped central areas of the plates are particularly unique in their applicability to the repair and recontour of the majority of large cranial defects in adult humans in four principal skull areas encompassing: 1) the frontal bone of the skull; 2) the right side parietal and temporal bones of the skull; 3) the left side parietal and temporal bones; and 4) the occipital bone and posterior portions of the right and left side parietal bones. These four skull areas form the principal cranial fields for the occurrence of depressed features, penetrating missile injuries, and intracranial tumor removal surgical procedures. Such areas also form the principal cranial fields requiring surgical correction of large congenital skull defects.

The implantable metallic cranioplasty plates of the invention are fabricated from thin sheets of commercially pure titanium or titanium alloys (finished thickness in the range of about 0.5 mm to about 1.5 mm) and preferably comprise mesh sheets which include uniform rows and lines of circular or square perforations for receiving titanium bone screws having low profile heads. The plate and panel perforations are created by techniques that result in the finished plates being free of mechanically induced stresses as are normally created by metal stamping, forging and mechanical machining procedures and techniques. The central convex preformed areas of the plates of the invention are created by the forming of such plate areas over dies which closely approximate the normal curvature areas of the skulls of human adult males and females as defined hereinbefore. The use of perforated titanium sheet mesh material with uniform lines and rows of square holes is preferred since the cranioplasty plates with square holes provide the surgeon with an implantable plate material which can be easily shaped or bent in the pliable peripheral panel areas to conform to the cranial bone surrounding the cranial defect without inducing mechanical stresses into the material. Also, the square hole perforated titanium sheet material of the plates in the peripheral panel areas can be easily cut or trimmed to fit the skull contour surrounding the defect site without leaving jagged plate edges. Another preferred form of perforated titanium (or titanium alloy) sheet material is comprised of a gridwork of legs which form repeating patterns of rectangular or triangular open spaces.

The implantable perforated titanium cranioplasty plates of the invention are radiolucent whereby the use of X-ray, CT and MRI examination of the skull behind the plates is not precluded or blocked and no imaging artifacts are created. Further, the perforated cranioplasty plates of the invention allow desired bio-fluid flow from side-to-side through the plates after their surgical placement and covering by outer soft tissues.

BRIEF DESCRIPTION OF THE DRAWING FIGURES

FIG. 1 is a top plan view of a perforated (square hole mesh) titanium cranioplasty plate preform of the present invention in its planer form prior to the application of anatomical convex shaping of the plate in its central skull defect covering area and prior to final adjustment contouring of the peripheral attachment panels of the plate during surgery for final fitment of the plate panels to norman cranial bone structures adjacent the skull defect;

Figure 4:
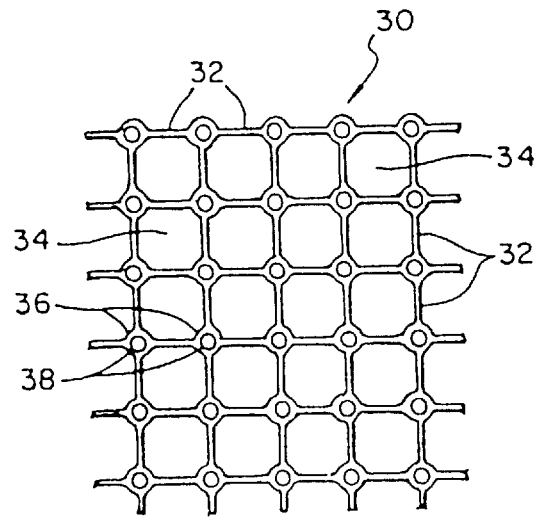
Figure 5:
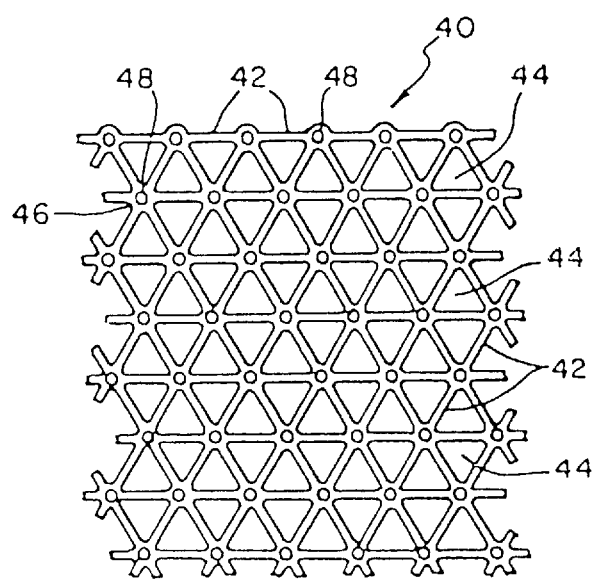

FIG. 4 is a plan view of a section of perforated metallic grid material of rectangular opening configuration applicable for use in forming cranioplasty plates in accordance with the present invention; and FIG. 5 is a plan view of a section of perforated metallic grid material of triangular opening configuration (isogrid material) applicable to use in forming cranioplasty plates in accordance with the invention.

DETAILED DESCRIPTION OF THE INVENTION

Figure 1:
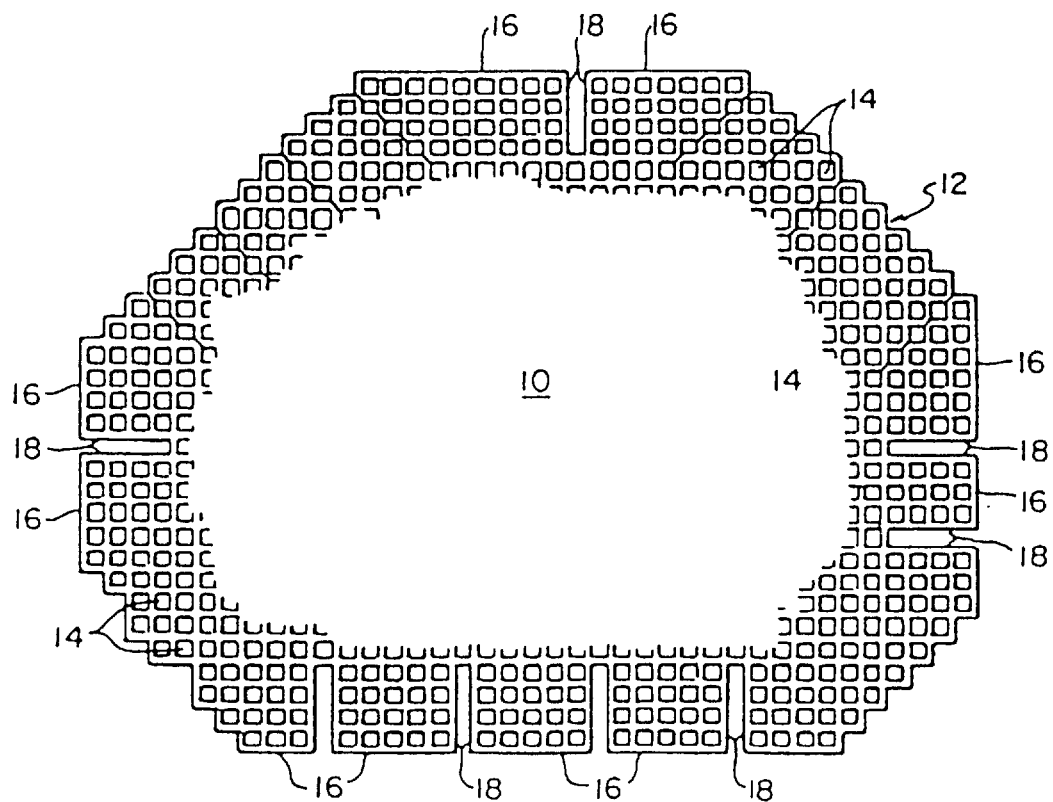

Referring to FIG. 1 of the drawing sheets there is illustrated a metallic cranioplasty plate preform 10 of the present invention. The plate preform 10 has been configured for shaping into an appropriately contoured cranioplasty plate for application over a large cranial defect encompassing contiguous areas of the left side parietal and temporal bones of the human skull. The plate preform, of generally elliptical shape, is formed of a pliable sheet 12 of commercially pure titanium (or titanium alloy) which has been perforated with uniform rows and lines of square holes 14. The preform 10 includes peripheral plate attachment panels 16 which are separated from one another by slots 18. Thus such panels may be easily shaped or bent, and trimmed, to conform to the cranial bone characteristics and curvatures surrounding the cranial defect which is to be protected by the finished and installed cranioplasty plate with the installed plate providing the desired restored contour of the skull throughout the area of the cranial defect.

Figure 2:
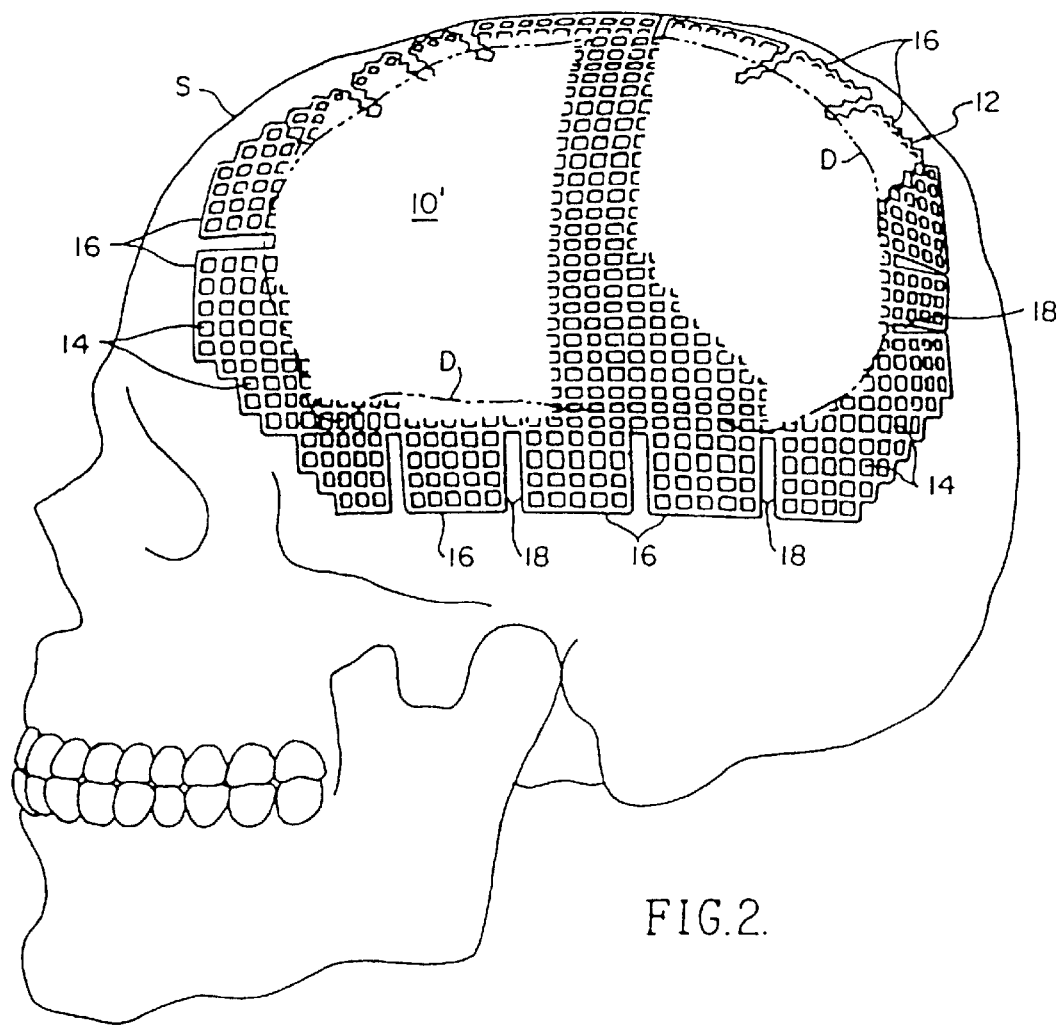
FIG. 2 is a side (lateral) view of a human skull showing the perforated metallic cranioplasty plate of FIG. 1 anatomically contoured and provided with adjusted slotted peripheral attachment panels for close cranial adaptation to cover and protect a large defect in the temporal and parietal bones on the left side of the skull.

In FIG. 2 there is illustrated a side (lateral) view of a human skull S showing a finished perforated metallic cranioplasty plate 10' formed from the plate preform 10 of FIG. 1. The preform plate 10 has been anatomically contoured for fitment to the skull over the contiguous cranial defect area encompassing the left side parietal and temporal bones and the peripheral attachment panels 16, separated from one-another by slots 18, have been bent inwardly as required to assure close fitment of the finished cranioplasty plate 10' to the skull. In the FIG. 2 illustration, bone screws have not been selectively applied through the square hole perforations of the attachment panels 16 for affixation of the cranioplasty plate prosthesis to the skull. Further, in FIG. 2 the shape of the cranial defect area D is shown in dashed outline.

Figure 3:
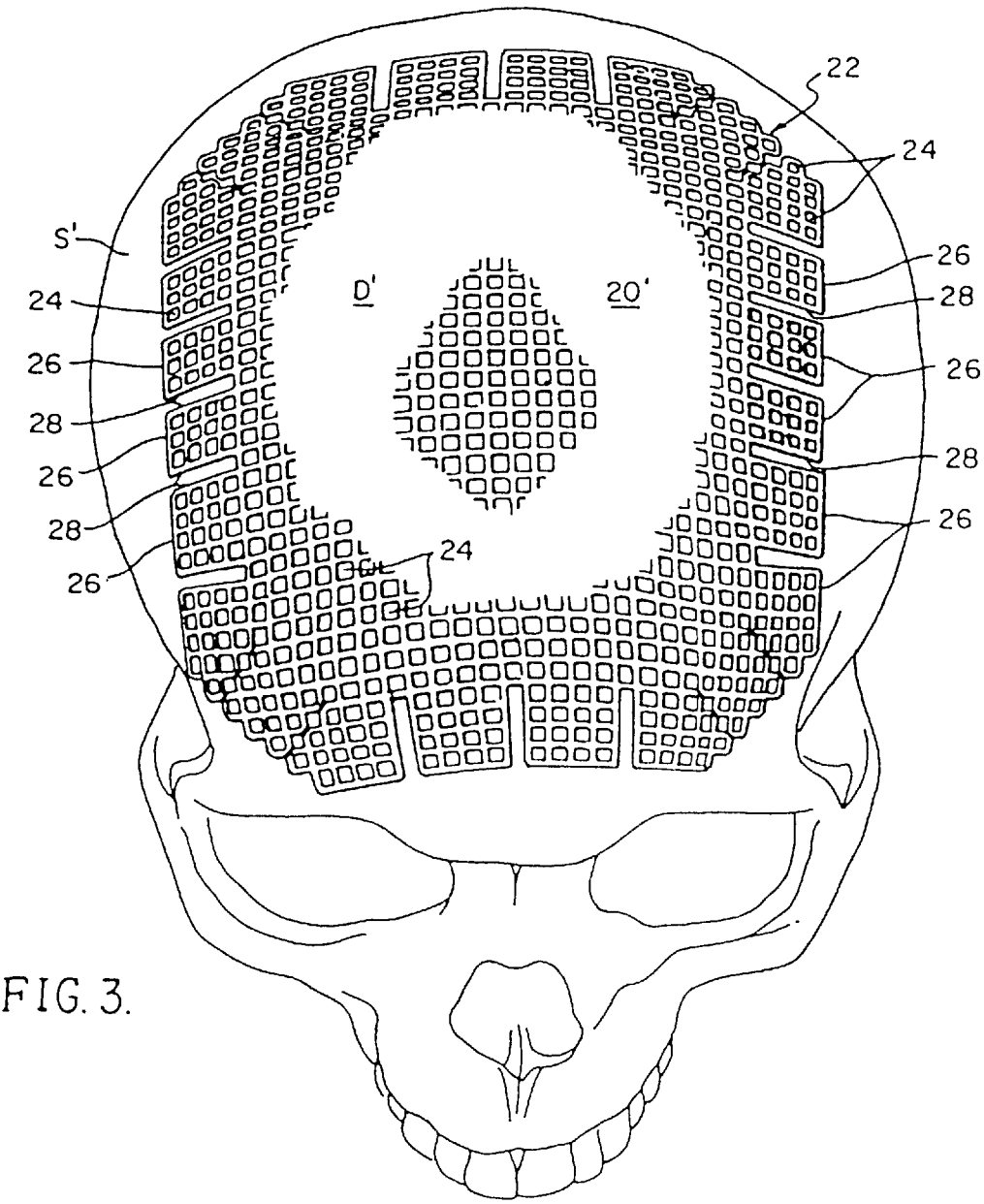
FIG. 3 is a front and top (frontal) perspective view of a human skull showing a perforated (square hole mesh) metallic cranioplasty plate of the invention anatomically contoured for close cranial adaptation to cover and protect a large defect in the frontal bone of the skull.

In FIG. 3 there is illustrated a front and top (frontal) perspective view of a human skull S' showing a finished perforated metallic cranioplasty plate structure 20' of the invention, the plate structure 20' having been formed from a plate preform 20 (not illustrated) of generally elliptical shape similar to the plate preform 10 of FIG. 1. The plate preform for the cranioplasty plate structure 20', formed of a pliable sheet 22 of commercially pure titanium with square hole perforations 24, has been anatomically contoured for fitment to the skull S' over a cranial defect area encompassing the frontal bone of the skull. The peripheral attachment panels 26 of the plate structure 20', separated from one-another by slots 28, have been bent inwardly as required to assure close fitment of the finished cranioplasty plate to the skull. In the FIG. 3 illustration, bone screws have not been selectively applied through the square hole perforations of the attachment panels 26 for affixation of the cranioplasty plate structure to the skull.

FIG. 4 is a plan view of a section of perforated metallic sheet material 30 comprised of a gridwork of legs 32 which form repeating patterns of rectangular open spaces 34, such material being applicable to use in forming cranioplasty plates in accordance with the present invention. The terminal ends of the legs 32 meet at, and are joined in, grid corners 36 which include holes 38 through which bone screws may be applied to affix the material to health bone at the periphery of a cranial defect. FIG. 5 is a plan view of a section of perforated metallic sheet material 40 comprised of a gridwork of legs 42 which form repeating patterns of triangular open spaces 44, such material also being applicable to use in forming cranioplasty plates in accordance with the invention. The terminal ends of the legs 42 meet at, and are joined in, grid corners 46 which include bone screw holes 48.

It is to be understood that the cranioplasty plates of the present invention are formed from a series of pliable metallic preforms (formed of biologically inert, commercially pure titanium or titanium alloy sheet material) which may be comprised of meshes having uniform parallel rows and perpendicularly oriented uniform lines of square hole or circular hole perforations or which are formed with repeating patterns of rectangular or triangular open gridwork. Preferably, such mesh perforations range in size from about 0.5 mm to about 3.0 mm in side dimension or diameter, respectively. The open spaces of the gridwork sheet material have defining legs which range in lengths from 3.0 mm to 8.0 mm or more. Also, the finished thickness of such preforms is in the range of from about 0.5 mm to about 1.5 mm and the preforms are of generally elliptical shape. They are provided with like perforated peripheral attachment panels separated from one-another by slots so that the edge portions of the finished cranioplasty plate can be shaped by the cranial surgeon at the time of plate application and fitment for recontour, closure and protection of a large cranial defect.

The perforated titanium cranioplasty plates of the invention include a preformed arcuate and convex central area within the confines of the pliable peripheral panels. The convex central areas of the plates are of a size and curvature shape which reasonably match the spheroidal shape and size of the majority of the skulls of adult human males and adult human females. Thus, the arcuate and convex shaped central areas of the plates are particularly unique in their particular applicability to the repair and recontour of the majority of large cranial defects in adult humans in four principal skull areas, i.e., spheroidal skull areas which encompass:

1) the frontal bone of the skull structure;
2) the contiguous areas of the right side parietal and temporal bones of the skull;
3) the contiguous areas of the left side parietal and temporal bones of the skull; and
4) the contiguous areas of the occipital bone and posterior portions of the right and left side parietal bones. These four skull areas comprise the principal cranial fields for the occurrence of depressed fractures, penetrating missile injuries, and intracranial tumor removal surgical procedures. Such areas also form the principal cranial fields requiring surgical correction of large congenital skull defects.

As previously indicated, the plate and panel perforations of the cranioplasty plates of the invention are created in the flat titanium (or titanium alloy) plate preforms by techniques that result in the finished plates being free of mechanically induced stresses as are normally created by metal stamping, forging and mechanical machining procedures and techniques. The central arcuate and convex preformed areas of the plates of the invention are created by forming of the plate preforms in their central areas over dies which closely approximate the normal four curvature areas of the typical skulls of adult males and females as defined hereinbefore.

The use of perforated titanium (or titanium alloy) sheet material with square holes is preferred since the cranioplasty plates with square holes provides the cranial surgeon with an implantable plate material which can be easily shaped or bent in the pliable peripheral panel areas to conform to the intact cranial bone surrounding the cranial defect area without inducing mechanical stresses into the material. Also, the square hole perforated titanium sheet material of the plates in the peripheral panel areas can be easily cut or trimmed to fit the skull contour surrounding the defect site without leaving jagged plate edges.

The implantable perforated titanium cranioplasty plates of the invention are radiolucent whereby the use of X-ray, CT and MRI examination of the repaired skull behind the plates is not precluded or blocked and no imaging artifacts are created. Further, the perforated cranioplasty plates of the invention allow desired bio-fluid flow from side-to-side through the plates after their surgical placement covering of the defect, attachment to the intact bone surrounding the defect, and covering by outer soft tissues.

While the invention has been described in connection with particular cranioplasty plate structures for use in the surgical repair and recontour of large cranial defects of the human skull, many modifications of the invention will be apparent to those skilled in the art. Accordingly, such modifications are to be included within the spirit and scope of the invention as defined by the following claims.

What is claimed is:

1. A cranioplasty plate for use in the repair and recontour of large cranial defects in the human skull, comprising:
    a sheet of perforated metallic material;
    said sheet including pliable peripheral panels for bending fitment of said sheet to bone surrounding the cranial defect; and
    said sheet having a central arcuate and convex portion with substantially increased rigidity in comparison to said pliable peripheral panels, said central portion configured to approximate the normal bone structure of a large cranial defect and to protect underlying tissue;
    wherein said sheet has a thickness in the range of about 0.5 mm to about 1.5 mm and includes uniform parallel rows and uniform parallel lines of perforations, said parallel lines of perforations being arranged generally perpendicular to said parallel rows of perforations.

2. The apparatus of claim 1 wherein said sheet is fabricated of commercially pure titanium or titanium alloy material.

3. The apparatus of claim 1 wherein said sheet includes perforations selected from the group consisting of square holes and circular holes.

4. The apparatus of claim 1 wherein said sheet is a gridwork sheet fabricated of biologically inert, commercially pure titanium or titanium alloy material having thickness in a range of about 0.5 mm to about 1.5 mm and legs which define rectangular perforations, the terminal ends of said legs meeting at, and joined in, grid corners which include holes adapted to receive screws.

5. The apparatus of claim 4 wherein said legs of said gridwork sheet define repeating patterns of rectangular perforations ranging in lengths from about 3.0 mm to about 8.0 mm.

6. The apparatus of claim 1 wherein said sheet is a gridwork sheet fabricated of biologically inert, commercially pure titanium or titanium alloy material having thickness in the range of about 0.5 mm to about 1.5 mm and legs which define triangular perforations, the terminal ends of said legs meeting at, and joined in, grid corners which include holes adapted to receive screws.

7. The apparatus of claim 6 wherein said legs of said gridwork sheet define repeating patterns of triangular perforations ranging in lengths from about 3.0 mm to about 8.0 mm.

8. The apparatus of claim 1 wherein:
said central portion is contoured to match the frontal bone of the skull structure.

9. The apparatus of claim 1 wherein:
said central portion is contoured to match the contiguous area of the right side parietal and temporal bones of the skull.

10. The apparatus of claim 1 wherein:
said central portion is configured to match the contiguous area of the left side parietal and temporal bones of the skull.

11. The apparatus of claim 1 wherein:
said central portion is configured to match the contiguous area of the occipital bone and posterior portions of the right and left side parietal bones.

12. A biocompatible cranioplasty plate structure for onlaid use in the surgical repair and recontour of a large cranial defect of the adult human skull, said plate structure comprising:

a perforated mesh sheet of biologically inert, commercially pure titanium or titanium alloy of generally elliptical configuration, said mesh sheet having a thickness in the range of about 0.5 mm to about 1.5 mm and including uniform parallel rows and uniform parallel lines of perforations, said parallel lines of perforations being arranged generally perpendicular to said parallel rows of perforations;

said mesh sheet including a central preformed arcuate and convex substantially rigid plate area matching the compound and complex curvature of the forehead, side or rear areas of the typical human adult skull; and said mesh sheet including a series of adjustable peripheral panels, extending radially from said rigid plate area and separated from one-another by radial slots, said peripheral panels for bending fitment and close adaptation of said mesh sheet to intact cranial bone of the skull adjacent to and surrounding said cranial defect.

* * * * *

UNITED STATES PATENT AND TRADEMARK OFFICE
CERTIFICATE OF CORRECTION

PATENT NO. : 5,814,048
DATED : September 29, 1998
INVENTOR(S) : Frank H. Morgan

It is certified that error appears in the above-identified patent and that said Letters Patent is hereby corrected as shown below:

In column 6, line 63 and 64, please delete "thickness in a range of about 0.5 mm to about 1.5 mm and".
In column 7, lines 7 and 8, please delete "thickness in the range of about 0.5 mm to about 1.5 mm and".

Signed and Sealed this

Seventeenth Day of August, 1999

Attest:

Q. TODD DICKINSON

Attesting Officer

Acting Commissioner of Patents and Trademarks